| United States Patent [19] | [11] 4,368,271 |
|---|---|
| Miura et al. | [45] Jan. 11, 1983 |

[54] PRODUCTION OF MICROBIAL CELLS FROM METHANOL

[75] Inventors: Yoshiharu Miura, 8-28, Katagiri-cho, Ibaraki-shi, Osaka 567, Japan; Mitsuo Okazaki, Kawanishi, Japan; Setsuo Komemushi, Osaka, Japan; Tenji Sakata, Suita, Japan; Satoshi Shiroza; Satoshi Obana, both of Ibaraki, Japan

[73] Assignees: Sekisui Kagaku Kogyo Kabushiki Kaisha; Yoshiharu Miura, both of Osaka, Japan

[21] Appl. No.: 212,082

[22] PCT Filed: Dec. 9, 1978

[86] PCT No.: PCT/JP78/00047

§ 371 Date: Aug. 9, 1980

§ 102(e) Date: Jul. 30, 1980

[87] PCT Pub. No.: WO80/01168

PCT Pub. Date: Jun. 12, 1980

[51] Int. Cl.³ .................. C12N 1/32; C12N 1/20; C12R 1/20

[52] U.S. Cl. .................. 435/247; 435/253; 435/804; 435/850

[58] Field of Search .............. 435/850, 873, 247, 248, 435/804, 253

[56] References Cited

U.S. PATENT DOCUMENTS

| 3,063,911 | 11/1962 | Tanaka et al. | 435/203 |
| 3,897,303 | 7/1975 | Sherk et al. | 435/247 |
| 3,965,985 | 6/1976 | Hitzman | 435/843 |
| 4,048,013 | 9/1977 | Wagner et al. | 435/247 |

*Primary Examiner*—David M. Naff
*Assistant Examiner*—Kathleen S. McCowin
*Attorney, Agent, or Firm*—Wenderoth, Lind & Ponack

[57] ABSTRACT

Microbial cells are produced in great quantities and good yield, and economically by cultivating a bacterium belonging to species selected from the group consisting of *Flavobacterium tosaensis, Pseudomonas wakayamaensis, Flavobacterium methanolicola, Corynebacterium yamanasiensis,* in a culture medium containing methanol as a major carbon source. Methanol is abundantly available from the chemical industry. The resultant microbial cells have a high protein content and can be utilized as feed, food, medical and industrial materials.

2 Claims, No Drawings

4,368,271

PRODUCTION OF MICROBIAL CELLS FROM METHANOL

FIELD OF TECHNOLOGY

This invention relates to a process for producing microbial cells. More specifically, it relates to a process for producing microbial cells economically in great quantities using novel microorganisms which aerobically assimilate methanol.

BACKGROUND ART

In recent years, much work has been done to develop methods for effectively utilizing microbial cells as feeds, foodstuffs, medicines, industrial materials, etc. To produce microbial cells with industrial advantages, methanol is expected to be used as a major carbon source because there is a good prospect that methanol will be supplied in great quantities and at low costs by the chemical industry. [See, for example, Japanese Laid-Open Patent Publications Nos. 14389/1972 and 15490/1978.]

DISCLOSURE OF THE INVENTION

In view of these circumstances, the present inventors widely searched in nature for microorganisms which would aerobically utilize methanol as a major carbon source and be able to be cultivated with good efficiency, and consequently discovered novel microorganisms, *Flavobacterium tosaensis, Pseudomonas wakayamaensis, Flavobacterium methanolicola, Pseudomonas kyotoensis, Pseudomonas aichiensis,* and *Corynebacterium yamanasiensis*. This led to the establishment of a process for producing microbial cells economically in large quantities by utilizing these microorganisms.

Thus, the present invention provides a process for producing microbial cells, which comprises cultivating a bacterium belonging to strains selected from the group consisting of *Flavobacterium tosaensis, Pseudomonas wakayamaensis, Flavobacterium methanolicola, Pseudomonas kyotoensis, Pseudomonas aichiensis* and *Corynebacterium yamanasiensis* in a culture medium containing methanol as a major carbon source, and recovering the microbial cells from the culture broth.

The microorganisms used in this invention have been determined to belong to the genus Pseudomonas, the genus Flavobacterium, or the genus Corynebacterium from their bacteriological characteristics. They have been identified as new strains because they differ in various respects from known bacteria belonging to the genus Flavobacterium, known bacteria belonging to the genus Pseudomonas and known bacteria belonging to the genus Corynebacterium, and also because the microorganisms of the genus Flavobacterium used in this invention can utilize methanol whereas known bacteria of the genus Flavobacterium have not been found to assimilate methanol. Thus, these microorganisms have been named *Flavoabacterium tosaensis, Pseudomonas wakayamaensis, Flavobacterium methanolicola, Pseudomonas kyotoensis, Pseudomonas aichiensis* and *Corynebacterium yamanasiensis*. Typical bacterial strains belonging to the novel microorganisms used in this invention are *Flavobacterium tosaensis* DS-1 [FERM-P No. 4058], *Flavobacterium methanolicola* DS-16 [FERM-P No. 4098], *Pseudomonas wakayamaensis* DS-25 [FERM-P No. 4100], *Pseudomonas kyotoensis* DS-22 [FERM-P No. 4099], *Pseudomonas aichiensis* DS-26 [FERM-P No. 4107], and *Corynebacterium yamanasiensis* DS-31 [FERM-P No. 4106], all of which are deposited in Fermentation Research Institute, Agency of Industrial Science and Technology, Japan at 5-8-1, Higashi, Inage, Chiba-ken, Japan.

The bacteriological properties of these bacterial strains are shown below.

[I] *Flavobacterium tosaensis* DS-1 [FERM-P No. 4058]:

(a) Morphology

Cultivated in a nutrient medium and a nutrient agar medium at 37° C. for 3 days.

(1) Shape and size of cells: Rods (0.5–0.75) by (1.6–2.2) microns
(2) Colonies of the cells: Single or pair
(3) Motility: None
(4) Spores: None
(5) Gram stain: Negative
(6) Acid-fastness: Negative (b) State of growth in various culture media (1) Nutrient agar plate culture: Growth abundant at 37° C. for 3 days. The colonies are circular with a diameter of 2–3 mm, and are convex or umbonate with a uniform structure, a smooth surface and an entire edge. Yellowish white or milky white, glistening translucent and mucoid.

(2) Methanol-containing agar plate culture: Growth is abundant at 37° C. for 3 days. The colonies are circular with a diameter of 2–2.5 mm, and are convex or umbonate with a smooth surface and an entire edge. White or opalescent, glistening, translucent and mucoid.

(3) Nutrient agar slant culture: Filiform growth at 37° C. for 3 days. The colonies have a smooth surface, and are moderately protruded with a yellowish white or milky white color and a glistening gloss. Translucent and mucoid.

(4) Methanol agar slant culture: Filiform growth at 37° C. for 3 days. The colonies have a smooth surface, and are moderately protruded with a white or opalescent color and a glistening gloss. Translucent and mucoid.

(5) Nutrient broth: Growth abundant at 37° C. for 3 days. The culture becomes turbid. Sediment is formed. A white ringed pellicle is formed on the surface.

(6) Peptone water broth: Growth abundant at 37° C. for 3 days. The culture becomes turbid. Sediment is formed. A ringed pellicle is formed on the surface.

(7) Methanol-containing broth: Growth abundant at 37° C. for 3 days. The culture becomes turbid. Sediment is formed. A ringed pellicle is formed on the surface.

(8) Nutrient broth [stabbed]: Growth is on the surface or proceeds to a 2–3 mm depth at 37° C. for 3 days.

(9) Nutrient gelatin broth [stabbed]: Surface growth at 30° C. for 5 days with sediment. Gelatin liquefied.

(10) Litmus milk: Acid is formed at 37° C. The culture turns red, and is coagulated.

(c) Biochemical properties (1) Reduction of nitrate: positive
(2) Denitrification reaction: positive
(3) MR test: negative
(4) VP test: positive
(5) Production of indole: negative
(6) Production of hydrogen sulfide: negative
(7) Hydrolysis of starch: negative
(8) Utilization of citrate (Koser's medium): negative (9) Utilization of inorganic nitrogen
Ammonium salt: positive
Nitrate: positive
(10) Production pf pigment (King's A and B media): negative
(11) Urease reaction: positive
(12) Oxidase reaction: positive
(13) Catalase reaction: positive
(14) Ranges of pH and temperature for growth in methanol-containing broth
pH range:
5–9 growth good
6–8 optimum
4 and 10 no growth
Temperature range:
5°–44° C. growth good
25°–42° C. optimum
45° C. no growth
(15) Relation to oxygen: Aerobic
(16) O-F test [by the Hugh Leifson method]: Oxidatively metabolizes glucose (weak formation of acid)
(17) Production of acid and gas from the following sugars (using peptone water in a sugar concentration of 1% at 37° C. for 10 days):

|  | Production of Acid | Production of Gas |
| --- | --- | --- |
| (1) L-Arabinose | + (weak) | − |
| (2) D-Xylose | − | − |
| (3) D-Glucose | + (weak) | − |
| (4) D-Mannose | + (weak) | − |
| (5) D-Fructose | + (weak) | − |
| (6) D-Galactose | + (weak) | − |
| (7) Maltose | + (weak) | − |
| (8) Sucrose | + (weak) | − |
| (9) Lactose | + (weak) | − |
| (10) Trehalose | + (weak) | − |
| (11) D-Sorbitol | − | − |
| (12) D-Mannitol | + (weak) | − |
| (13) Inositol | − | − |
| (14) Glycerin | + (weak) | − |
| (15) Starch | + (weak) | − |

(18) Assimilation of sugars (using sugar in place of methanol in the methanol containing broth in a concentration of 1% at 37° C. for 10 days):

| Sugar | Assimilation |
| --- | --- |
| (1) L-Arabinose | + (weak) |
| (2) D-Xylose | + (weak) |
| (3) D-Glucose | + (weak) |
| (4) D-Mannose | + (weak) |
| (5) D-Fructose | + (weak) |
| (6) D-Galactose | + (weak) |
| (7) Maltose | + (weak) |
| (8) Sucrose | + (weak) |
| (9) Lactose | + (weak) |
| (10) Trehalose | + (weak) |
| (11) D-Sorbitol | − |
| (12) D-Mannitol | + (weak) |
| (13) Inositol | + |
| (14) Glycerin | + (weak) |
| (15) Starch | + (weak) |

(d) Source of isolation: Soil

The methanol-containing agar medium and the methanol-containing broth used in the cultivation tests above are as follows:
(1) Methanol-containing agar medium
$KH_2PO_4$: 1.5 g
$Na_2HPO_4$: 3.2 g
$(NH_4)_2SO_4$: 3 g
$MgSO_4.7H_2O$: 0.5 g
$CaCl_2.2H_2O$: 0.1 g
$FeSO_4.7H_2O$: 0.01 g
$ZnSO_4.7H_2O$: 1.4 mg
$CuSO_4.5H_2O$: 0.25 mg
$Na_2MoO_4.2H_2O$: 0.24 mg
$CoCl_2.6H_2O$: 0.24 mg
$MnSO_4.5H_2O$: 1.2 mg
Agar: 20 g
Distilled water: 1 l A culture medium consisting of the above ingredients was sterilized at 120° C. for 15 minutes, and then 20 g of methanol was aseptically added thereto.
(2) Methanol-containing broth The same medium as the methanol containing agar medium above except that 20 g of agar was not used and the amount of methanol used was changed to 5 g.

[II] *Pseudomonas wakayamaensis* DS-25 (FERM-P No. 4100):
(a) Morphology

Cultivated in a nutrient broth and a nutrient agar medium at 37° C. for 3 days.
(1) Shape and size of cells: Rods, (0.3–0.4) by (2.0–2.2) microns.
(2) Colonies of the cells: Single or pair
(3) Motility: Motile with polar flagella.
(4) Spores: None
(5) Gram stain: Negative
(6) Acid-fastness: Negative
(b) State of growth in various culture media
(1) Nutrient agar plate culture: Growth abundant at 37° C. for 3 days. The colonies are circular having diameter of 3–4 mm with rough surface, lobate edge, milky yellowish white color. Cretaceous, translucent and mucoid.
(2) Methanol-containing agar plate culture: Growth abundant at 37° C. for 5 days. The colonies are circular having a diameter of 3–4 mm, and are protruded in an umbilicate shape (concave at the center). Rough surface, entire edge, opalescent color, and glistening gloss. Translucent and mucoid.
(3) Nutrient agar slant culture: Filiform growth at 37° C. for 3 days. The colonies have a smooth surface, and are moderately protruded. Wave-like or lobate edge, milky yellowish white color, and dull gloss. Translucent and mucoid.
(4) Methanol-containing agar slant culture: Filiform growth at 37° C. for 5 days. The colonies are moderately protruded and have a smooth surface. Entire edge, opalescent color, and glistening gloss. Translucent and mucoid.
(5) Nutrient broth: Growth moderate at 37° C. for 3 days. No sediment formed. A pellicle is formed on the surface.
(6) Nutrient broth (shaken): Growth abundant at 37° C. for 3 days. The culture becomes turbid. Sediment is formed. Translucent.
(7) Peptone water broth (shaken): Growth abundant at 37° C. for 3 days. The culture becomes turbid. Sediment is formed.
(8) Methanol-containing broth: Growth abundant at 37° C. for 3 days. The culture becomes turbid. Sediment is formed. A thin ringed pellicle is formed on the surface. Translucent.

(9) Methanol-containing broth (shaken): Growth abundant at 37° C. for 3 days. The culture becomes turbid. Sediment is formed. Translucent.

(10) Nutrient broth (stabbed): Growth is on the surface or proceeds to a 1-3 mm depth at 37° C. for 3 days. Surface milky yellowish white.

(11) Nutrient gelatin broth (stabbed): Surface growth at 30° C. for 5 days with sediment. Gelatin liquefied.

(12) Litmus milk: At 37° C., the culture is coagulated.

(c) Biochemical properties
  (1) Reduction of Nitrate: positive
  (2) Denitrification reaction: negative
  (3) MR test: negative
  (4) VP test: positive
  (5) Production of indole: negative
  (6) Production of hydrogen sulfide: negative
  (7) Hydrolysis of starch: positive
  (8) Utilization of citrate (Koser's medium): positive
  (9) Utilization of inorganic nitrogen
    Ammonium salt: positive
    Nitrate: positive
  (10) Production of pigment (King's A and B media): negative
  (11) Urease reaction: positive
  (12) Oxidase reaction: positive
  (13) Catalase reaction: positive
  (14) Ranges for growth: The temperature and pH are varied in the methanol-containing broth described hereinbelow (pH was adjusted by adding an aqueous solution of NaOH or HCl). Growth good at a pH in the range of 6 to 9. No growth at a pH of 5 and 10. Growth good at a temperature of 5° to 40° C. The optimum temperature is 25° to 40° C. No growth at 41° C.
  (15) Relation to oxygen: Aerobic
  (16) O-F test (by the Hugh Leifson method): Oxidatively metabolizes glucose.
  (17) Production of acid and gas from the following sugars (using peptone water in a sugar concentration of 1 wt % at 37° C. for 10 days):

|  | Production of Acid | Production of Gas |
| --- | --- | --- |
| (1) L-Arabinose | − | − |
| (2) D-Xylose | − | − |
| (3) D-Glucose | + | − |
| (4) D-Mannose | + | − |
| (5) D-Fructose | + | − |
| (6) D-Galactose | − | − |
| (7) Maltose | + | − |
| (8) Sucrose | + | − |
| (9) Lactose | − | − |
| (10) Trehalose | + | − |
| (11) D-Sorbitol | − | − |
| (12) D-Mannitol | + | − |
| (13) Inositol | − | − |
| (14) Glycerin | + | − |
| (15) Starch | + | − |

(18) Assimilation of sugars (using sugar in place of methanol in the methanol-containing broth 0.5 wt % at 37° C. for 10 days):

|  | Assimilation |
| --- | --- |
| (1) L-Arabinose | + |
| (2) D-Xylose | + |
| (3) D-Glucose | + (weak) |
| (4) D-Mannose | + |
| (5) D-Fructose | + (weak) |
| (6) D-Galactose | + (weak) |
| (7) Maltose | + |
| (8) Sucrose | + (weak) |
| (9) Lactose | − |
| (10) Trehalose | + |
| (11) D-Sorbitol | + |
| (12) D-Mannitol | + |
| (13) Inositol | + |
| (14) Glycerin | + |
| (15) Starch | + |

(d) Source of isolation: Soil

The methanol-containing agar medium and the methanol-containing broth used in the cultivation tests above are as follows:

(1) Methanol-containing agar medium
  $KH_2PO_4$: 1.5 g
  $Na_2HPO_4$: 3.2 g
  $(NH_4)_2SO_4$: 3 g
  $MgSO_4.7H_2O$: 0.5 g
  $CaCl_2.2H_2O$: 0.1 g
  $FeSO_4.7H_2O$: 0.01 g
  $ZnSO_4.7H_2O$: 1.4 mg
  $CuSO_4.5H_2O$: 0.25 mg
  $Na_2MoO_4.2H_2O$: 0.24 mg
  $CoCl_2.6H_2O$: 0.24 mg $MnSO_4.5H_2O$: 1.2 mg Agar: 20 g
  Distilled water: 1 l A culture medium consisting of the above ingredients was sterilized at 120° C. for 15 minutes, and then 20 g of methanol was aseptically added thereto.

(2) Methanol-containing broth

The same medium as the methanol-containing agar medium above except that 20 g of agar was not used and the amount of methanol used was changed to 5 g.

[III] *Flavobacterium methanolicola* DS-16 (FERM-P No. 4098):

(a) Morphology

Cultivated in a nutrient broth and a nutrient agar medium at 37° C. for 3 days.
  (1) Shape and size of cells: Rods, (0.5–0.7) by (1.5–1.8) microns.
  (2) Colonies of the cells: Single or pair.
  (3) Motility: None
  (4) Spores: None
  (5) Gram stain: Negative
  (6) Acid-fastness: Negative (b) State of growth in various culture media
  (1) Nutrient agar plate culture: Growth abundant at 37° C. for 3 days. The colonies are circular with a diameter of 4–5 mm. The protrusion is convex or umbonate. Uniform structure, smooth surface, and entire edge. Yellowish-brown, glistening, translucent and mucoid.
  (2) Methanol-containing agar plate culture: Growth abundant at 37° C. for 5 days. The colonies are circular having a diameter of 2–3 mm. The protrusion is convex. Smooth surface, entire edge, milky yellowish-white color, and glistening gloss. Translucent and mucoid.
  (3) Nutrient agar slant culture: Filiform growth at 37° C. for 3 days. The colonies are moderately protruded with a rough surface and an entire edge. Yellowish-brown, glistening, translucent and mucoid.

(4) Methanol-containing agar slant culture: Filiform growth at 37° C. for 5 days. The colonies are moderately protruded with a smooth surface and an entire edge. Milky yellowish-white, glistening, translucent and mucoid.
(5) Nutrient broth: Growth moderate at 37° C. for 3 days. Sediment is formed. A pellicle is formed on the surface.
(6) Nutrient broth (shaken): Growth abundant at 37° C. for 3 days. The culture becomes turbid. Sediment is formed. Translucent.
(7) Peptone water broth (shaken): Growth abundant at 37° C. for 3 days. The culture becomes turbid. Sediment is formed.
(8) Methanol-containing broth: Growth abundant at 37° C. for 3 days. The culture becomes turbid. Sediment is formed. A thin ringed pellicle is formed on the surface. Translucent.
(9) Methanol-containing broth (shaken): Growth abundant at 37° C. for 3 days. The culture becomes turbid. Sediment is formed. Translucent.
(10) Nutrient broth (stabbed): Growth is on the surface or proceeds to a 3–5 mm depth at 37° C. for 3 days. Surface yellowish-brown.
(11) Nutrient gelatin broth (stabbed): At 30° C. for 5 days, no gelatin liquefaction occurs.
(12) Litmus milk: At 37° C., the culture is coagulated.

[C] Biochemical properties
(1) Reduction of nitrate: positive
(2) Denitrification reaction: positive
(3) MR test: negative
(4) VP test: positive
(5) Production of indole: negative
(6) Production of hydrogen sulfide: negative
(7) Hydrolysis of starch: positive
(8) Utilization of citrate (Koser's medium): positive
(9) Utilization of inorganic nitrogen
  Ammonium salt: positive
  Nitrate: positive
(10) Production of pigment (King's A and B media): negative
(11) Urease reaction: positive
(12) Oxidase reaction: positive
(13) Catalase reaction: positive
(14) Ranges for growth: The temperature and pH are varied in the methanol-containing broth described hereinbelow. (The pH is adjusted by adding an aqueous solution of NaOH or HCl.) Growth good at a pH of 5 to 9. A pH range of 6 to 8 is preferred. No growth at a pH of 4 and 10. Growth good at a temperature of 15° to 40° C. Temperatures of 25° to 40° C. are preferred. No growth at 42° C.
(15) Relation to oxygen: Aerobic
(16) O-F test (by the Hugh Leifson method): Oxidatively metabolizes glucose.
(17) Production of acid and gas from the following sugars (using peptone water in a sugar concentration of 1 wt % at 37° C. for 10 days):

|  | Production of Acid | Production of Gas |
| --- | --- | --- |
| (1) L-Arabinose | + (weak) | − |
| (2) D-Xylose | − | − |
| (3) D-Glucose | + (weak) | − |
| (4) D-Mannose | + (weak) | − |
| (5) D-Fructose | + (weak) | − |
| (6) D-Galactose | − | − |
| (7) Maltose | − | − |
| (8) Sucrose | + (weak) | − |
| (9) Lactose | − | − |
| (10) Trehalose | + (weak) | − |
| (11) D-Sorbitol | − | − |
| (12) D-Mannitol | + | − |
| (13) Inositol | − | − |
| (14) Glycerin | + | − |
| (15) Starch | − | − |

(18) Assimilation of sugars (using sugar in place of methanol in the methanol-containing broth in a concentration of 0.5 wt % at 37° C. for 10 days):

|  | Assimilation |
| --- | --- |
| (1) L-Arabinose | + (weak) |
| (2) D-Xylose | + (weak) |
| (3) D-Glucose | + (weak) |
| (4) D-Mannose | + (weak) |
| (5) D-Fructose | + (weak) |
| (6) D-Galactose | + (weak) |
| (7) Maltose | + (weak) |
| (8) Sucrose | + (weak) |
| (9) Lactose | − |
| (10) Trehalose | + |
| (11) D-Sorbitol | + |
| (12) D-Mannitol | + (weak) |
| (13) Inositol | + (weak) |
| (14) Glycerin | + (weak) |
| (15) Starch | + (weak) |
| (d) Source of isolation: Soil |  |

The methanol-containing agar medium and the methanol-containing broth used in the cultivation tests above are as follows:

(1) Methanol-containing agar medium
$KH_2PO_4$: 1.5 g
$Na_2HPO_4$: 3.2 g
$(NH_4)_2SO_4$: 3 g
$MgSO_4.7H_2O$: 0.5 g
$CaCl_2.2H_2O$: 0.1 g
$FeSO_4.7H_2O$: 0.01 g
$ZnSO_4.7H_2O$: 1.4 mg
$CuSO_4.5H_2O$: 0.25 mg
$Na_2MoO_4.2H_2O$: 0.24 mg
$CoCl_2.6H_2O$: 0.24 mg
$MnSO_4.5H_2O$: 1.2 mg
Agar: 20 g
Distilled water: 1 l A culture medium consisting of the above ingredients was sterilized at 120° C. for 15 minutes, and then 20 g of methanol was aseptically added thereto.

(2) Methanol-containing broth
The same medium as the methanol containing agar medium above except that 20 g of agar was not used and the amount of methanol used was changed to 5 g.

[IV] *Pseudomonas kyotoensis* DS-22 (FERM-P No. 4099):
(a) Morphology
Cultivated in a nutrient broth and a nutrient agar medium at 37° C. for 3 days.
(1) Shape and size of cells: Rods, (0.5)×(1.7–1.8) microns.
(2) Colonies of the cells: Single or pair.
(3) Motility: Motile with polar flagella.
(4) Spores: None
(5) Gram stain: Negative
(6) Acid-fastness: Negative (b) State of growth in various culture media
  (1) Nutrient agar plate culture: Growth abundant at 37° C. for 3 days. The colonies are circular having a diameter of 3-4 mm with a smooth surface and an entire or wave-like edge. Milky yellowish-white, cretaceous, translucent and mucoid.
  (2) Methanol-containing agar plate culture: Growth abundant at 37° C. for 5 days. The colonies are circular having a diameter of 3-4.5 mm, and protruded in an umbilicate shape with a rough surface and an entire edge. Opalescent, cretaceous, translucent and mucoid.
  (3) Nutrient agar slant culture: Filiform growth at 37° C. for 3 days. The colonies are moderately protruded, with a smooth surface and an entire or wave-like edge. Milky yellowish white, cretaceous, translucent and mucoid.
  (4) Methanol-containing agar slant culture: Filiform growth at 37° C. for 5 days. The colonies are moderately protruded with a rough surface and a wave-like or lobate edge, and are opalescent. A pale pink pigment formed. Very dull gloss. Translucent and mucoid.
  (5) Nutrient broth: Growth moderate at 37° C. for 3 days. No sediment is formed. A pellicle is formed on the surface.
  (6) Nutrient broth (shaken): Growth abundant at 37° C. for 3 days. The culture becomes turbid. Sediment is formed. Translucent.
  (7) Peptone water broth (shaken): Growth abundant at 37° C. for 3 days. The culture becomes turbid. Sediment is formed.
  (8) Methanol-containing broth: Growth abundant at 37° C. for 3 days. The culture becomes turbid. Sediment is formed. A thin pellicle is formed on the surface. Translucent.
  (9) Methanol-mineral salts broth (shaken): Growth abundant at 37° C. for 3 days. The culture becomes turbid. Sediment is formed. Translucent.
  (10) Nutrient broth (stabbed): At 37° C. for 3 days, the growth is only on the surface. Milky yellow surface.
  (11) Nutrient gelatin broth (stabbed): Surface growth at 30° C. for 5 days with sediment. Gelatin liquefied.
  (12) Litmus milk: At 37° C., the culture is coagulated.
(c) Biochemical properties
  (1) Reduction of nitrate: positive
  (2) Denitrification reaction: negative
  (3) MR test: negative
  (4) VP test: positive
  (5) Production of indole: negative
  (6) Production of hydrogen sulfide: negative
  (7) Hydrolysis of starch: positive
  (8) Utilization of citrate (Koser's medium): positive
  (9) Utilization of inorganic nitrogen
    Ammonium salt: positive
    Nitrate: positive
  (10) Production of pigment (King's A and B media: negative
  (11) Urease reaction: positive
  (12) Oxidase reaction: positive
  (13) Catalase reaction: positive
  (14) Ranges for growth: The temperature and pH are varied in the methanol-containing broth described hereinbelow (pH is adjusted by adding an aqueous solution of NaOH or HCl). Good growth at a pH in the range of 5 to 9. A pH of 6 to 8 is preferred. No growth at a pH of 4 and 10. Good growth at a temperature of 5° to 45° C. Temperatures of 25° to 42° C. are preferred. No growth at 48° C.
  (15) Relation to oxygen: Aerobic
  (16) O-F test (by the Hugh Leifson method): Oxidatively metabolizes glucose.
  (17) Production of acid and gas from the following sugars (using peptone water in a sugar concentration of 1 wt % at 37° C. for 10 days):

|  | Production of Acid | Production of Gas |
|---|---|---|
| (1) L-Arabinose | − | − |
| (2) D-Xylose | − | − |
| (3) D-Glucose | + | − |
| (4) D-Mannose | + | − |
| (5) D-Fructose | + | − |
| (6) D-Galactose | − | − |
| (7) Maltose | + | − |
| (8) Sucrose | + | − |
| (9) Lactose | − | − |
| (10) Trehalose | + | − |
| (11) D-Sorbitol | + (weak) | − |
| (12) D-Mannitol | + | − |
| (13) Inositol | − | − |
| (14) Glycerin | + | − |
| (15) Starch | + | − |

(18) Assimilation of sugars (using sugar in place of methanol in the methanol-containing broth medium in a concentration of 0.5 wt % at 37° C. for 10 days):

|  | Assimilation |
|---|---|
| (1) L-Arabinose | + |
| (2) D-Xylose | + |
| (3) D-Glucose | + |
| (4) D-Mannose | + |
| (5) D-Fructose | + (weak) |
| (6) D-Galactose | + |
| (7) Maltose | + |
| (8) Sucrose | + |
| (9) Lactose | − |
| (10) Trehalose | + |
| (11) D-Sorbitol | + |
| (12) D-Mannitol | + |
| (13) Inositol | + |
| (14) Glycerin | + |
| (15) Starch | + |

(d) Source of isolation: Soil

The methanol-containing agar medium and the methanol-containing broth used in the cultivation tests above are as follows:
(1) Methanol-containing agar medium
  $KH_2PO_4$: 1.5 g
  $Na_2HPO_4$: 3.2 g
  $(NH_4)_2SO_4$: 3 g
  $MgSO_4.7H_2O$: 0.5 g
  $CaCl_2.2H_2O$: 0.1 g
  $FeSO_4.7H_2O$: 0.01 g
  $ZnSO_4.7H_2O$: 1.4 g
  $CuSO_4.5H_2O$: 0.25 mg
  $Na_2MoO_4.2H_2O$: 0.24 mg
  $CoCl_2.6H_2O$: 0.24 mg
  $MnSO_4.5H_2O$: 1.2 mg
  Agar: 20 g
  Distilled water: 1 l A culture medium consisting of the above ingredients was sterilized at 120° C. for 15 minutes, and then 20 g of methanol was aseptically added thereto.

(2) Methanol-containing broth

The same medium as the methanol-containing agar medium above except that 20 g of agar was not used and the amount of methanol used was changed to 5 g.

(V) *Pseudomonas aichiensis* DS-26 (FERM-P No. 4107):

(a) Morphology

Cultivated in a nutrient broth and a nutrient agar medium at 37° C. for 3 days.
 (1) Shape and size of cells: Rods, (0.3–0.4) by (0.75–1.0) microns.
 (2) Colonies of the cells: Single or pair.
 (3) Motility: Motile with polar flagella.
 (4) Spores: None
 (5) Gram stain: Negative
 (6) Acid-fastness: Negative (b) State of growth in various culture media
 (1) Nutrient agar plate culture: Growth abandant at 37° C. for 3 days. The colonies are circular having a diameter of 4–6 mm with an umbilicate shape, a smooth surface and an entire or lobate edge. Milky yellowish white, glistening, translucent and mucoid.
 (2) Methanol-containing agar plate culture: Growth is abundant at 37° C. for 5 days. The colonies are circular having a diameter of 2–3 mm with a smooth surface and an entire edge. Opalescent, glistening, translucent and mucoid.
 (3) Nutrient agar slant culture: Filiform growth at 37° C. for 3 days. The colonies are moderately protruded with a smooth surface and an entire or wave-like edge. Milky yellowish-white, glistening, translucent and butyrous.
 (4) Methanol-containing agar slant culture: Filiform growth at 37° C. for 5 days. The colonies are moderately protruded with a smooth surface and an entire edge. Opalescent, glistening, translucent and butyrous.
 (5) Nutrient broth: Growth abundant at 37° C. for 3 days. Sediment is formed. Translucent. A pellicle is formed on the surface.
 (6) Nutrient broth (shaken): Growth abundant at 37° C. for 3 days. The culture becomes turbid. Sediment is formed. Translucent.
 (7) Peptone water broth (shaken): Growth abundant at 37° C. for 3 days. The culture becomes turbid. Sediment is formed.
 (8) Methanol-containing broth: Growth is abundant at 37° C. for 3 days. The culture becomes turbid. Sediment is formed. A thin ringed pellicle is formed on the surface. Translucent.
 (9) Methanol-containing broth (shaken): Growth abundant at 37° C. for 3 days. The culture becomes turbid. Sediment is formed. Translucent.
 (10) Nutrient broth (stabbed): Growth is on the surface or proceeds to a 2–3 mm depth at 37° C. for 3 days. Milky white surface.
 (11) Nutrient gelatin broth (stabbed): Surface growth at 37° C. for 5 days with sediment. Gelatin liquefied.
 (12) Litmus milk: At 37° C., the culture is coagulated.

(c) Biochemical properties
 (1) Reduction of nitrate: negative
 (2) Denitrification: negative
 (3) MR test: negative
 (4) VP test: positive
 (5) Production of Indole: negative
 (6) Production of hydrogen sulfide: negative
 (7) Hydrolysis of starch: negative
 (8) Utilization of citrate (Koser's medium): negative
 (9) Utilization of inorganic nitrogen
  Ammonium salt: positive
  Nitrate: negative
 (10) Production of pigment (King's A and B media): negative
 (11) Urease reaction: positive
 (12) Oxidase reaction: positive
 (13) Catalase reaction: positive
 (14) Ranges for growth: The temperature and pH are varied (the pH is adjusted by adding an aqueous solution of NaOH or HCl). Growth good at a pH in the range of 5 to 9, but no growth at a pH of 4 and 10. Growth good at a temperature of 5° to 45° C., and temperature at 25° to 43° C. are preferred. No growth at 50° C.
 (15) Relation to oxygen: Aerobic
 (16) O-F test (by the Hugh Leifson method): Glucose is neither aerobically nor anaerobically metabolized. (no formation of acid and gas)
 (17) Production of acid and gas from the following sugars (using peptone water in a sugar concentration of 1 wt % at 37° C. for 10 days):

|  | Production of Acid | Production of Gas |
| --- | --- | --- |
| (1) L-Arabinose | + (weak) | − |
| (2) D-Xylose | − | − |
| (3) D-Glucose | + (weak) | − |
| (4) D-Mannose | + (weak) | − |
| (5) D-Fructose | + (weak) | − |
| (6) D-Galactose | − | − |
| (7) Maltose | − | − |
| (8) Sucrose | + (weak) | − |
| (9) Lactose | − | − |
| (10) Trehalose | + (weak) | − |
| (11) D-Sorbitol | − | − |
| (12) D-Mannitol | + | − |
| (13) Inositol | − | − |
| (14) Glycerin | + | − |
| (15) Starch | − | − |

(18) Assimilation of sugars (using sugar in place of methanol in the methanol-containing broth medium in a concentration of 0.5 wt % at 37° C. for 10 days):

|  | Assimilation |
| --- | --- |
| (1) L-Arabinose | + (very weak) |
| (2) D-Xylose | + (very weak) |
| (3) D-Glucose | + (very weak) |
| (4) D-Mannose | + (very weak) |
| (5) D-Fructose | + (very weak) |
| (6) D-Galactose | + (very weak) |
| (7) Maltose | + (very weak) |
| (8) Sucrose | + (very weak) |
| (9) Lactose | − |
| (10) Trehalose | + (very weak) |
| (11) D-Sorbitol | − |
| (12) D-Mannitol | + (very weak) |
| (13) Inositol | + (weak) |
| (14) Glycerin | + (very weak) |
| (15) Starch | − |

(d) Source of isolation: Soil

The methanol-containing agar medium and the methanol-containing broth used in the cultivation tests above are as follows:
 (1) Methanol-containing agar medium
  $KH_2PO_4$: 1.5 g
  $Na_2HPO_4$: 3.2 g (NH$_4$)$_2$SO$_4$: 3 g
MgSO$_4$.7H$_2$O: 0.5 g
CaCl$_2$.2H$_2$O: 0.1 g
FeSO$_4$.7H$_2$O: 0.01 g
ZnSO$_4$.7H$_2$O: 1.4 mg
CuSO$_4$.5H$_2$O: 0.25 mg
Na$_2$MoO$_4$.2H$_2$O: 0.24 mg
CoCl$_2$.6H$_2$O: 0.24 mg
MnSO$_4$.5H$_2$O: 1.2 mg
Agar: 20 g
Distilled water: 1 l A culture medium consisting of the above ingredients was sterilized at 120° C. for 15 minutes, and then 20 g of methanol was aseptically added thereto.

(2) Methanol-containing broth

The same medium as the methanol-containing agar medium above except that 20 g of agar was not used and the amount of methanol used was changed to 5 g.

(VI) *Corynebacterium yamanasiensis* DS-31 (FERM-P No. 4106):

(a) Morphology

Cultivated in a nutrient broth and a nutrient agar medium at 37° C. for 3 days.

(1) Shape and size of cells: Short rods, (0.5–0.6) by (0.6–0.9) micron.
(2) Colonies of the cells: Single or pair, and pleomorphic or curved and V-shaped divided cells.
(3) Motility: None
(4) Spores: None
(5) Gram stain: Positive
(6) Acid-fastness: Negative (b) State of growth on various culture media (1) Nutrient agar plate culture: Growth abundant at 37° C. for 3 days. The colonies are circular having a diameter of 2–2.5 mm, and a convex or umbonate with a smooth surface and entire edge. Yellow, glistening, translucent and butyrous.
(2) Methanol-containing agar plate culture: Growth abundant at 37° C. for 5 days. The colonies are circular having a diameter of 2–3 mm with a smooth surface and an entire edge. Opalescent, glistening, translucent and butyrous.
(3) Nutrient agar slant culture: Filiform growth at 37° C. for 3 days. The colonies are moderately protruded with a smooth surface and an entire edge. Yellow, glistening, translucent and butyrous.
(4) Methanol-containing agar slant culture: Filiform growth at 37° C. for 5 days. The colonies are moderately protruded with a smooth surface and an entire edge. Opalescent, glistening, translucent and butyrous.
(5) Nutrient broth: Growth moderate at 37° C. for 3 days. Sediment is formed. Slightly translucent. No ringed pellicle nor pellicle is formed on the surface.
(6) Nutrient broth (shaken): Growth abundant at 37° C. for 3 days. The culture becomes turbid. Sediment is formed. Translucent.
(7) Peptone water broth: Growth abundant at 37° C. for 3 days. The culture becomes turbid. Sediment is formed.
(8) Methanol-containing broth: Growth abundant at 37° C. for 3 days. The culture becomes turbid. Sediment is formed. A thin ringed pellicle is formed on the surface. Translucent.
(9) Methanol-containing broth (shaken): Growth abundant at 37° C. for 3 days. The culture becomes turbid. Sediment is formed. Translucent.
(10) Nutrient broth (stabbed): Growth is on the surface or proceeds to a 2–3 mm depth at 37° C. for 3 days. Opalescent surface.
(11) Nutrient gelatin broth (stabbed): Surface growth at 30° C. for 5 days with sediment. No gelatin liquefaction.
(12) Litmus milk: At 37° C., the culture is coagulated.

(c) Biochemical properties (1) Reduction of nitrate: positive
(2) Denitrification reaction: positive
(3) MR test: positive
(4) VP test: positive
(5) Production of indole: negative
(6) Production of hydrogen sulfide: negative
(7) Hydrolysis of starch: positive
(8) Utilization of citrate (Koser's medium): negative
(9) Utilization of inorganic nitrogen
   Ammonium salt: positive
   Nitrate: positive
(10) Production of pigment (King's A and B media): negative
(11) Urease reaction: negative
(12) Oxidase reaction: negative
(13) Catalase reaction: positive
(14) Ranges for growth: The temperature and pH are varied in the methanol-containing broth described hereinbelow (the pH is adjusted by adding an aqueous solution of HCl or NaOH). Good growth at a pH in the range of 5 to 9, but no growth at a pH of 5 and 10. Good growth at a temperature of 5° to 41° C., and temperatures of 25° to 40° C. are preferred. No growth at 42° C.
(15) Relation to oxygen: Aerobic
(16) O-F test (by the Hugh Leifson method): Glucose is neither aerobically nor anaerobically metabolized. (no formation of acid and gas)
(17) Production of acid and gas from the following sugars (using peptone water in a sugar concentration of 1 wt % at 37° C. for 10 days):

|  | Production of Acid | Production of Gas |
| --- | --- | --- |
| (1) L-Arabinose | − | − |
| (2) D-Xylose | − | − |
| (3) D-Glucose | + | − |
| (4) D-Mannose | + | − |
| (5) D-Fructose | + | − |
| (6) D-Galactose | + | − |
| (7) Maltose | + | − |
| (8) Sucrose | + | − |
| (9) Lactose | + | − |
| (10) Trehalose | + (weak) | − |
| (11) D-Sorbitol | − | − |
| (12) D-Mannitol | − | − |
| (13) Inositol | − | − |
| (14) Glycerin | + | − |
| (15) Starch | − | − |

(18) Assimilation of sugars (using sugar in place of methanol in the methanol-containing broth medium in a concentration of 0.5 wt % at 37° C. for 10 days):

|  | Assimilation |
| --- | --- |
| (1) L-Arabinose | + |
| (2) D-Xylose | + (weak) |
| (3) D-Glucose | + (weak) |
| (4) D-Mannose | + (weak) |
| (5) D-Fructose | + (weak) |

-continued

| | Assimilation |
|---|---|
| (6) D-Galactose | + (weak) |
| (7) Maltose | + (weak) |
| (8) Sucrose | + (weak) |
| (9) Lactose | + (weak) |
| (10) Trehalose | + |
| (11) D-Sorbitol | − |
| (12) D-Mannitol | + (weak) |
| (13) Inositol | + |
| (14) Glycerin | + (weak) |
| (15) Starch | − |

(d) Source of isolation: Soil

The methanol-containing agar medium and the methanol-containing broth used in the cultivation tests above are as follows:

(1) Methanol-containing agar medium $KH_2PO_4$: 1.5 g
$Na_2HPO_4$: 3.2 g
$(NH_4)_2SO_4$: 3 g
$MgSO_4.7H_2O$: 0.5 g
$CaCl_2.2H_2O$: 0.1 g
$FeSO_4.7H_2O$: 0.01 g
$ZnSO_4.7H_2O$: 1.4 mg
$CuSO_4.5H_2O$: 0.25 mg
$Na_2MoO_4.2H_2O$: 0.24 mg
$CoCl_2.6H_2O$: 0.24 mg
$MnSO_4.5H_2O$: 1.2 mg
Agar: 20 g
Distilled water: 1 l A culture medium consisting of the above ingredients was sterilized at 120° C. for 15 minutes, and then 20 g of methanol was aseptically added thereto.

(2) Methanol-containing broth

The same medium as the methanol-containing agar medium above except that 20 g of agar was not used and the amount of methanol used was changed to 5 g.

The above experiments were performed in accordance with "Bergey's Manual of Determinative Bacteriology", 8th edition (1974), "Manual of Practical Bacteriology" (edited by Alumni Association of the Institute of Medical Science, revised edition published in 1975 by Maruzen Co., Ltd.) and "Taxonomy and Determination of Microorganisms" (edited and written by Takeji Hasegawa, published in 1975 by Tokyo University Press).

That the above six bacterial strains used in this invention are novel was judged from the following facts taken in conjunction with the above bacteriological properties.

(A) A study of the bacteriological properties of *Flavobacterium tosaensis* DS-1 in accordance of the taxonomical standards described in Bergey's Manual of Determinative Bacteriology, 8th edition (1974) shows this strain to resemble closely the genus Flavobacterium because it is rod-shaped, Gram-negative, aerobic and non-motile, grows on a nutrient broth, does not form spores, forms acid from glucose, and does not ferment lactose. The difference from the genus Flavobacterium resides in the fact that the colonies of the present strain are not yellow but milky yellow or opalescent. If this strain is determined to belong to a genus other than the genus Flavobacterium, its properties do not correspond to those of any of the genera described in Section I-101, 102 and 103 of the Key to Genera of Manual, in the aforesaid Bergey's Manual. Accordingly, this strain has been determined to be a bacterium of the genus Flavobacterium.

When the present strain is compared with the principal 12 species of the genus Flavobacterium described in the Bergey's Manual in respect of the properties tabulated in this book, it is seen that *Flavobacterium ferrugineum* and *Flavobacterium rigense* are least different from the present strain.

On further cmparison of the present strain with these two species in regard also to the other properties described in the test of the Bergey's Manual, it is seen that the present strain differs from *Flavobacterium ferrugineum* in hydrolysis of starch and growth on a broth-agar medium, and from *Flavobacterium rigense* in motility, growth in litmus milk, and behavior toward oxygen. Furthermore, no other known literature reference discloses a bacterium having the same properties as the present strain. Accordingly, the present strain has been determined to be a novel strain of the genus Flavobacterium.

(B) A study of *Pseudomonas wakayamaensis* DS-25 in accordance with the taxonomical standards described in the Bergey's Manual shows it to belong to the genus Pseudomonas.

The present strain has been compared with the principal 29 species of the genus Pseudomonas described in this Manual in regard to the properties tabulated in this book. On comparison of properties other than the utilization of carbon sources, the present strain is considered to be closest to *Pseudomonas facilis* because it has flagella, does not grow at 41° C., and liquefies gelatin. However, when the present strain is compared with *Pseudomonas facilis* in all properties including the utilization of carbon sources, they are different in regard to not only the utilization of methanol, which is characteristic of the present strain, but also the hydrolysis of starch, the utilization of lactose, and the utilization of sucrose.

Relatively analogous strains disclosed in other known literature references are *Pseudomonas methanoloxidans* described in Japanese Laid-Open Patent Publication No. 6192/74, *Pseudomonas aeruginosa* described in Japanese Laid-Open Patent Publication No. 154480/75, and *Pseudomonas methanolitica* described in Japanese Laid-Open Patent Publication No. 41490/76.

The present strain, however, differs from *Pseudomonas methanoloxidans* in regard to the reduction of nitrate, the positive urease reaction, the growth temperature and pH ranges, formation of acids from many kinds of sugars, and the utilization of lactose; from *Pseudomonas aeruginosa* in regard to the negative result of the MR test, the positive result of the VP test, the growth temperature and pH ranges, the degree of growth in a stationary nutrient broth culture, the absence of sediment, and the non-utilization of lactose; and from *Pseudomonas methanolitica* in regard to the absence of hydrogen sulfide formation, the hydrolysis of starch, the utilization of citric acid, the growth temperature and pH ranges, the formation of acids form many kinds of sugars, and the non-utilization of lactose.

Thus, it has been ascertained that the present strain differs greatly from any known strains of the genus Pseudomonas. Accordingly, the present strain has been determined to be a novel stran of the genus Pseudomonas.

(C) A study of the bacteriological properties of *Flavobacterium methanolicola* DS-16 in accordance with the taxonomical standards in the Bergey's Manual shows it to be closest to the genus Flavobacterium because it is rod-shaped, Gram-negative, aerobic and non-motile, grows on a nutrient broth medium, does not form spores, forms acid from glucose, and does not ferment lactose. The difference of this strain from the genus Flavobacterium resides in the fact that the colonies of the present strain are not yellow but yellowish brown. If it is assumed to be of other genera than the genus Flavobacterium in view of the difference in colony, its properties do not correspond with those of any of the genera described in Section I-101, 102, and 103 of Key to Genera of Manual of the Bergey's Manual. Accordingly, the present strain has been determined to be a bacterium belonging to the genus Flavobacterium.

When the present strain is compared with the principal 12 species of the genus Flavobacterium described in the Bergey's Manual in the properties tabulated in this book, it is seen that *Flavobacterium breve* and *Flavobacterium rigense* are least different from the present strain. A further detailed comparison of the present strain with these strains in regard to all properties including the properties described in the text of the Bergey's Manual shows that the present strain differs from *Flavobacterium breve* in regard to the formation of acid from maltose, the utilization of citrate, and growth on a broth agar culture medium; and from *Flavobacterium rigense* in motility, the liquefaction of gelatin, growth in litmus milk, and behavior toward oxygen. Moreover, no other known literature reference discloses a strain having the same properties as the present strain. Accordingly, this strain has been determined to be a novel strain of the genus Flavobacterium.

(D) A study of the bacteriological properties of *Pseudomonas kyotoensis* DS-22 in accordance with the taxonomical standards described in the Bergey's Manual shows it to belong to the genus Pseudomonas.

The present strain has been compared with the principal 29 species of the genus Pseudomonas classified in the Bergey's Manual in regard to the properties tabulated in this book. In properties other than the utilization of carbon sources, the present strain is considered to be closest to *Pseudomonas alcaligenes* because it has flagella, grows at 41° C., is negative in a denitrification reaction, and liquefies gelatin. However, when the present strain is compared with *Pseudomonas alcaligenes* in regard to all properties including utilization of carbon sources, it is seen that they are different not only in the utilization of methanol which is characteristic of the present strain, but also in the hydrolysis of starch and the utilization of glucose, trehalose and inositol.

Relatively analogous strains disclosed in other known literature references are *Pseudomonas methacarbohylis* disclosed in Japanese Laid-Open Patent Publication No. 71886/75, *Pseudomonas methanoloxidans* disclosed in Japanese Laid-Open Patent Publication No. 6192/74, and *Pseudomonas methanolitica* disclosed in Japanese Laid-Open Patent Publication No. 41490/76.

However, the present strain differs from *Pseudomonas methacarbohylis* because it does not form hydrogen sulfide, utilizes citrate, forms acids from many kinds of sugars, utilizes L-arabinose, inositol and glycerol, and does not utilize lactose; from *Pseudomonas methanoloxidans* because its reduction of nitrate is positive and its urease reaction is positive, its growth temperature is different, it forms acids from many kinds of sugars, and it utilizes lactose; and from *Pseudomonas methanolitica* because it does not form hydrogen sulfide, hydrolyzes starch, utilizes citrate, forms acids from many kinds of sugars and utilizes lactose and its growth temperature is different.

Thus, the present strain has been determined to be very different from any of the known strains of the genus *Pseudomonas*. Accordingly, the present strain has been determined to be a new strain of the genus *Pseudomonas*.

(E) A study of the bacteriological properties of *Pseudomonas aichiensis* DS-26 in accordance with the taxonomical standards described in the Bergey's Manual has shown it to belong to the genus *Pseudomonas*.

The present strain has been compared with the principal 29 species of the genus *Pseudomonas* classified in the above book in regard to the properties tabulated in the above book. As a result, the present strain is considered to be closest to *Pseudomonas alcaligenes* because it has flagella, grows at 41° C., liquefies gelatin, and does not hydrolyze starch. However, when the present strain is compared with *Pseudomonas alcaligenes* in all of the properties including assimilability, they are different not only in the utilization of methanol which is characteristics of the present strain but also in the growth temperature and the utilization of glucose, trehalose and inositol.

Relatively analogous strains disclosed in other known literature references are *Pseudomonas methanoloxidans* in Japanese Laid-Open Patent Publication No. 6192/72 and *Pseudomonas methanolitica* in Japanese Laid-Open Patent Publication No. 41490/76. However, the present strain differs from *Pseudomonas methanoloxidans* in regard to urease reaction, the growth temperature, the formation of acids from many kinds of sugars, and the utilization of lactose, D-sorbitol and starch; and from *Pseudomonas methanolitica* in regard to the reduction of nitrate, the formation of hydrogen sulfide, the growth temperature, the formation of acids from many kinds of sugars, and the utilization of lactose, D-sorbitol and starch.

Thus, it has been confirmed that the present strain markedly differs from any known strains of the genus *Pseudomonas*. Accordingly, the present strain has been determined to be a novel strain of the genus *Pseudomonas*.

(F) A study of the bacteriological properties of *Corynebacterium yamanasiensis* DS-31 in accordance with the taxonomical standards described in the Bergey's Manual has shown it to be of the genus *Corynebacterium* because it is of short-rod-shaped, Gram stain positive, non-motile and aerobic, does not have flagella and it is seen to have irregularly-shaped or curved cells and V-shape divided cells.

The present strain has been compared with the species of the genus *Corynebacterium* which are described in Section I and II of the Bergey's Manual in regard to properties other than the utilization of carbon sources and the formation of acids and gases from sugars. It cannot be compared with the species described in Section III of the Bergey's Manual because it does not describe properties.

On comparison with regard to the presence of flagella, Gram-stain, catalase reaction, indole reaction, urease reaction, the hydrolysis of starch, the reduction of nitrate, the liquefaction of gelatin, growth in litmus milk, oxidase reaction, and the growth temperature range, the present strain is considered to be close to *Corynebacterium pseudotuberculosis*, *Corynebacterium, xerosis*, *Corynebacterium bovis*, *Corynebacterium enzymi-* cum, Corynebacterium murisepticum, Corynebacterium nephridi, and Corynebacterium diphteriae.

The present strain cannot be fully differentiated from Corynebacterium enzymicum and Corynebacterium nephridi because there are a very few properties described, but an apparent difference is that these strains do not utilize methanol. The present strain differs from Corynebacterium pseudotuberculosis in regard to the utilization of methanol and the liquefaction of gelatin; from Corynebacterium bovis in regard to the utilization of methanol and oxidase reaction although only a few properties are described; from Corynebacterium murisepticum in regard to the utilization of methanol, the formation of hydrogen sulfide, growth in litmus milk, and the formation of acid from D-mannitol; and from Corynebacterium diphteriae in regard to the utilization of methanol and the formation of acid from sucrose.

A relatively analogous strain described in another known literature reference is Corynebacterium methanophilum described in Japanese Laid-Open Patent Publication No. 41490/76. It has been ascertained, however, that the present strain differs markedly from Corynebacterium methanophilum in regard to the growth temperature and pH ranges, the formation of hydrogen sulfide, the hydrolysis of starch, the formation of indole, the reduction of nitrate, urease reaction, VP test, MR test, the formation of acids from many kinds of sugars, and the utilization of many carbon sources.

Accordingly, this strain has been determined to be a novel strain of the genus Corynebacterium.

In the cultivation of the microorganism in accordance with this invention, an aerobic liquid cultivation method is suitable. The cultivation temperature is 5° to 45° C., preferably 25° to 43° C. The pH of the cultivation system is 5 to 9, preferably 6 to 8. The cultivation can be performed either batchwise or continuously.

Methanol is used as a major carbon source in the culture medium. The preferred amount of methanol is not more than 50 g/liter.

The nitrogen sources used are inorganic substances such as ammonium salts and nitrates and organic substances such as urea, casein, corn steep liquor, peptone, yeast extract and meat extract. Phosphorus sources are phosphate salts, and useful sulfur sources are sulfate salts. As a source of a metal such as magnesium, potassium, calcium, sodium, iron, manganese, copper, zinc, molybdenum, cobalt and boron, a suitable amount of a salt of the corresponding metal is added. If required, a substance required indispensably for the growth of microbial cells such as vitamins and amino acids, or a growth promoting material is added.

The culture medium may be a natural culture medium if it contains methanol, nitrogen sources, inorganic substances, and substances essential for growth such as vitamims and amino acids or suitable amounts of growth promoting substances. The pH of the culture medium can be conveniently adjusted by a phosphate and ammonia.

Recovery of microbial cells from the culture broth can be effected in a customary manner, for example, by filtration, centrifugal separation, etc. Washing and drying can also be applied.

According to this invention, methanol supplied abundantly by the chemical industry can be utilized as a major carbon source, and microbial cells of strains belonging to Flavobacterium tosaensis, Pseudomonas wakayamaensis, Flavobacterium methanolicola, Pseudomonas kyotoensis, Pseudomona saichiensis, and Corynebacterium yamanasiensis can be produced in great quantities and in good yields. Since the microbial cells obtained contain much proteins, they can be utilized not only as feeds and foods, but also as materials for medicines and industrial materials.

BEST MODE OF PRACTICING THE INVENTION

The following Examples further illustrate the present invention.

EXAMPLE 1

$KH_2PO_4$: 1.5 g
$Na_2HPO_4$: 3.2 g
$(NH_4)_2SO_4$: 3 g
$MgSO_4.7H_2O$: 0.5 g
$CaCl_2.2H_2O$: 0.1 g
$FeSO_4.7H_2O$: 0.02 g
$ZnSO_4.7H_2O$: 2.8 mg
$CuSO_4.5H_2O$: 0.5 mg
$Na_2MoO_4.2H_2O$: 0.48 mg
$CoCl_2.6H_2O$: 0.48 mg
$MnSO_4.5H_2O$: 2.4 mg
Distilled water: 1 l A culture medium (500 ml) consisting of the above ingredients was placed in a 1-liter small jar, and sterilized at 120° C. for 15 minutes. Then, 5 g of methanol was aseptically added. Into the resulting culture medium was inoculated 2% by volume of a preculture containing the cells of Flavobacterium tosaensis DS-1 (FERM-P No. 4058) which had been obtained by precultivation in a culture medium having the same composition as above at 37° C. for 24 hours. Cultivation was performed at 37° C. for 20 hours with aeration and stirring while maintaining the pH of the culture medium at 7.0 by 13% by weight ammonia solution. The culture broth was centrifuged to separate the microbial cells. The cells were washed with water, and dried at 100° C. for 24 hours to obtain dried cells at a rate of 4.5 g per liter of the culture broth. The generation time of this culture in the logarithmic growth period was 1.4 hours. The cells were found to contain 80% by weight of crude proteins.

EXAMPLE 2

A culture medium (1.2 l) having the same composition as in Example 1 was placed in a 2.5-l jar fermentor, and sterilized at 120° C. for 20 minutes. Then, 12 g of methanol was added aseptically. To the resulting culture medium was inoculated 5% by volume of a preculture containing the cells of Flavobacterium tosaensis DS-1 (FERM-P No. 4058) which has been obtained by precultivation at 37° C. for 20 hours in a culture medium having the same composition as in Example 1. Cultivation was performed at 37° C. with aeration and stirring while maintaining the pH of the culture medium at 7.0 using 13% by weight ammonia solution. At the end of 20 hours from the beginning of cultivation, the concentration of the cells was 4.5 g/l. Per liter of the culture broth, the following aqueous metal salt solutions were added.

18 ml of a 10% by weight aqueous solution of $KH_2PO_4$,
77 ml of a 5% by weight aqueous solution of $Na_2HPO_4$,
18 ml of a 10% by weight aqueous solution of $MgSO_4.7H_2O$, 3.5 ml of a 10% by weight aqueous solution of $CaCl_2.2H_2O$, 5 ml of a 1% by weight aqueous solution of $FeSO_4.7H_2O$, 4 ml of a 1% by weight aqueous solution of $ZnSO_4.7H_2O$, 0.7 ml of a 1% by weight aqueous solution of $CuSO_4.5H_2O$, 1.1 ml of a 1% by weight aqueous solution of $MnSO_4.5H_2O$, 2 ml of a 0.1% by weight aqueous solution of $H_3BO_3$, and 0.5 ml of a 0.1% by weight aqueous solution of $CoCl_2.6H_2O$.

Twenty hours after the beginning of cultivation, methanol was automatically added so that the concentration of methanol in culture broth was maintained at 1 to 5 g/l thereafter. The amount of methanol added at the end of 29 hours after the beginning of cultivation reached 96 g per liter of the culture broth. At the end of 29 hours after the cultivation, the culture broth was centrifuged to separate the microbial cells. The cells were washed with water, and dried at 100° C. for 24 hours to afford 32 g of dried cells per liter of the culture broth. The cells were found to contain 77% by weight of crude proteins.

EXAMPLE 3

$KH_2PO_4$: 1.5 g
$Na_2HPO_4$: 3.2 g
$(NH_4)_2SO_4$: 3 g
$MgSO_4.7H_2O$: 0.5 g
$CaCl_2.2H_2O$: 0.1 g
$FeSO_4.7H_2O$: 0.02 g
$ZnSO_4.7H_2O$: 2.8 mg
$CuSO_4.5H_2O$: 0.5 mg
$Na_2MoO_4.2H_2O$: 0.48 mg
$CoCl_2.6H_2O$: 0.48 mg
$MnSO_4.5H_2O$: 2.4 mg
Distilled water: 1 l A culture medium (100 ml) consisting of the above ingredients were put into a 0.5 liter Sakaguchi flask, and sterilized at 120° C. for 15 minutes. Then, 0.2 g of methanol was aseptically added. Into the resulting culture medium was inoculated 0.5% by volume of a pre-culture containing the cells of *Pseudomonas wakayamaensis* DS-25 (FERM-P No. 4100) which had been obtained by precultivation at 35° C. for 24 hours in a culture medium having the same composition as above except that the amount of methanol was changed to 0.5% by weight. Cultivation was carried out at 35° C. for 24 hours under shaking. The culture broth was centrifuged to separate the microbial cells. The cells were washed with water, and dried at 100° C. for 24 hours to form 0.9 g of dried cells per liter of the culture broth. The generation time of this culture in the logarithmic growth period was 1.5 hours. The cells were found to contain 78% by weight of crude proteins.

EXAMPLE 4

A culture medium (500 ml) having the same composition as in Example 3 was placed into a 1-l small jar, and sterilized at 120° C. for 15 minutes. Then, 5 g of methanol was added aseptically. Into the resulting culture medium was inoculated 2% by volume of a preculture containing the cells of *Pseudomonas wakayamaensis* DS-25 (FERM-P No. 4100) which had been obtained by pre-cultivation at 37° C. for 24 hours in a culture medium having the same composition as above. Cultivation was performed at 37° C. for 20 hours while maintaining the pH of the culture medium at 7.0 using 13% by weight ammonia solution.

The culture broth was centrifuged to separate the microbial cells. The cells were washed with water, and dried at 100° C. for 24 hours to afford 4.2 g of dried cells per liter of the culture broth. The generation time of this culture in the logarithmic growth period was 1.6 hours. The cells were found to contain 78% by weight of crude proteins.

EXAMPLE 5

$KH_2PO_4$: 1.5 g
$Na_2HPO_4$: 3.2 g
$(NH_4)_2SO_4$: 3 g
$MgSO_4.7H_2O$: 0.5 g
$CaCl_2.2H_2O$: 0.1 g
$FeSO_4.7H_2O$: 0.02 g
$ZnSO_4.7H_2O$: 2.8 mg
$CuSO_4.5H_2O$: 0.5 mg
$Na_2MoO_4.2H_2O$: 0.48 mg
$CoCl_2.6H_2O$: 0.48 mg
$MnSO_4.5H_2O$: 2.4 mg
Distilled water: 1 l A culture medium (100 ml) consisting of the above ingredients was placed into a 0.5 liter Sakaguchi flask, and sterilized at 120° C. for 15 minutes. Then, 0.2 g of methanol was aseptically added. Into the resulting culture medium was inoculated 0.5% by volume of a pre-culture containing the cells of *Flavobacterium methanolicola* DS-16 (FERM-P No. 4098) which had been obtained by pre-cultivation at 35° C. for 24 hours in a culture medium having the same composition as above except that the amount of methanol added was changed to 0.5% by volume. Cultivation was performed at 35° C. for 24 hours with shaking.

The culture broth was centrifuged to separate the microbial cells. The cells were washed with water, and dried at 100° C. for 24 hours to afford 0.85 g of dried cells per liter of the culture broth.

The generation time of this culture in the logarithmic growth period was 1.5 hours. The cells were found to contain 75% by weight of crude proteins.

EXAMPLE 6

A culture medium (500 ml) having the same composition as in Example 5 was placed into a 1-l small jar, and sterilized at 120° C. for 15 minutes. Then, 5 g of methanol was added aseptically. Into the resulting culture medium was inoculated 2% by volume of a preculture containing the cells of *Flavobacterium methanolicola* DS-16 (FERM-P No. 4098) which had been obtained by pre-cultivation at 37° C. for 24 hours in a culture medium having the same composition as above. Cultivation was performed at 37° C. for 20 hours with aeration and stirring while maintaining the pH of the culture medium at 7.0 by using 13% by weight ammonia solution.

The culture broth was centrifuged to separate the microbial cells. The cells were washed with water, and dried at 100° C. for 24 hours to afford 4.2 g of dried cells per liter of the culture broth. The generation time of this culture in the logarithmic growth period was 1.6 hours. The cells were found to contain 78% by weight of crude proteins.

EXAMPLE 7

KH$_2$PO$_4$: 1.5 g
Na$_2$HPO$_4$: 3.2 g
(NH$_4$)$_2$SO$_4$: 3 g
MgSO$_4$.7H$_2$O: 0.5 g
CaCl$_2$.2H$_2$O: 0.1 g
FeSO$_4$.7H$_2$O: 0.02 g
ZnSO$_4$.7H$_2$O: 2.8 mg
CuSO$_4$.5H$_2$O: 0.5 mg
Na$_2$MoO$_4$.2H$_2$O: 0.48 mg
CoCl$_2$.6H$_2$O: 0.48 mg
MnSO$_4$.5H$_2$O: 2.4 mg
Distilled water: 1 l A culture medium (500 ml) consisting of the above ingredients was placed into a 1-l small jar, and sterilized at 120° C. for 15 minutes. Then, 5 g of methanol was aseptically added. Into the resulting culture medium was inoculated 2% by volume of a pre-culture containing the cells of *Pseudomonas kyotoensis* DS-22 (FERM-P No. 4099) which had been obtained by pre-cultivation at 37° C. for 24 hours in a culture medium having the same composition as above. Cultivation was performed at 37° C. for 20 hours with aeration and stirring while maintaining the pH of the culture medium at 7.0 by using 13% by weight ammonia solution. The culture broth was centrifuged to separate the microbial cells. The cells were washed with water, and dried at 100° C. for 24 hours to afford 4.3 g of dried cells per liter of the culture broth. The generation time of this culture in the logarithmic growth period was 1.5 hours. The cells were found to contain 79% by weight of crude proteins.

EXAMPLE 8

A culture medium (1.2 l) having the same composition as in Example 7 was placed into a 2.5-l jar fermentor, and sterilized at 120° C. for 20 minutes. Then, 12 g of methanol was added aseptically. Into the resulting culture medium was inoculated 5% by volume of a pre-culture containing the microbial cells of *Pseudomonas kyotoensis* DS-22 (FERM-P No. 4099) which had been obtained by pre-cultivation at 37° C. for 24 hours in a culture medium having the same composition as above. Cultivation was performed at 37° C. with aeration and stirring while maintaining the pH of the culture medium at 7.0 by using 13% by weight of ammonia solution.

At the end of 20 hours after the beginning of cultivation, the concentration of the cells was 4.3 g/l. Per liter of the culture broth were added the following aqueous metal salt solutions.

18 ml of a 10% by weight aqueous solution of KH$_2$PO$_4$,
77 ml of a 5% by weight aqueous solution of Na$_2$HPO$_4$,
18 ml of a 10% by weight aqueous solution of MgSO$_4$.7H$_2$O,
3.5 ml of a 10% by weight aqueous solution of CaCl$_2$.2H$_2$O,
5 ml of a 1% by weight aqueous solution of FeSO$_4$.7H$_2$O,
3 ml of a 1% by weight aqueous solution of ZnSO$_4$.7H$_2$O,
0.6 ml of a 1% by weight aqueous solution of CuSO$_4$.5H$_2$O,
0.7 ml of a 1% by weight aqueous solution of MnSO$_4$.5H$_2$O, and
2 ml of a 0.1% by weight aqueous solution of H$_2$BO$_3$.

Twenty hours after the initiation of the cultivation, methanol was automatically added so that its concentration in the culture broth was maintained at 1 to 5 g/liter thereafter. The total amount of added methanol at the end of 32 hours after the initiation of cultivation reached 92 g/liter of the culture broth. At the end of 32 hours after the initiation of cultivation, the culture broth was centrifuged to separate the microbial cells. The cells were washed with water, and dried at 100° C. for 24 hours to afford 31 g of dried cells per liter of the culture broth. The cells were found to contain 78% by weight of crude proteins.

EXAMPLE 9

KH$_2$PO$_4$: 1.5 g
Na$_2$HPO$_4$: 3.2 g
(NH$_4$)$_2$SO$_4$: 3 g
MgSO$_4$.7H$_2$O: 0.5 g
CaCl$_2$.2H$_2$O: 0.1 g
FeSO$_4$.7H$_2$O: 0.02 g
ZnSO$_4$.7H$_2$O: 2.8 mg
CuSO$_4$.5H$_2$O: 0.5 mg
Na$_2$MoO$_4$.2H$_2$O: 0.48 mg
CoCl$_2$.6H$_2$O: 0.48 mg
MnSO$_4$.5H$_2$O: 2.4 mg
Distilled water: 1 l A culture medium (100 ml) consisting of the above ingredients was put into a 0.5-l Sakaguchi flask, and sterilized at 120° C. for 15 minutes. Then, 0.2 g of methanol was aseptically added. Into the resulting culture medium was inoculated 0.5% by volume of pre-culture containing the microbial cells of *Pseudomonas aichiensis* DS-26 (FERM-P No. 4107) which had been obtained by pre-cultivation at 37° C. for 24 hours in a culture medium having the same composition as above except that the amount of methanol was changed to 0.5% by weight. Cultivation was performed at 37° C. for 24 hours with shaking. The culture broth was centrifuged to separate the microbial cells. The cells were washed with water, and dried at 100° C. for 24 hours to afford 0.88 g of dried cells per liter of the culture broth. The generation time of this culture at the logarithmic growth period was 1.5 hours. The cells were found to contain 79% by weight of crude proteins.

EXAMPLE 10

A culture medium (500 ml) having the same composition as in Example 9 except that the amount of methanol added was changed to 5 g was placed into a 1-l small jar, and sterilized at 120° C. for 15 minutes. Then, methanol in the amount indicated above was aseptically added. Into the resulting culture medium was inoculated 2% by volume of a pre-culture containing the cells of *Pseudomonas aichiensis* DS-26 (FERM-P No. 4107) which had been obtained by pre-cultivation at 37° C. for 24 hours in a culture medium having the same composition as in Example 9. Cultivation was carried out at 37° C. for 20 hours with aeration and stirring while maintaining the pH of the culture medium at 7.0 by using 13% by weight ammonia solution.

The culture broth was centrifuged to separate the microbial cells. The cells were washed with water, and dried at 100° C. for 24 hours to afford 4.1 g of dried cells per liter of the culture broth. The generation time of this culture in the logarithmic growth period was 1.6 hours. The cells were found to contain 79% by weight of crude proteins.

EXAMPLE 11

KH$_2$PO$_4$: 1.5 g
Na$_2$HPO$_4$: 3.2 g
(NH$_4$)$_2$SO$_4$: 3 g
MgSO$_4$.7H$_2$O: 0.5 g
CaCl$_2$.2H$_2$O: 0.1 g
FeSO$_4$.7H$_2$O: 0.02 g
ZnSO$_4$.7H$_2$O: 2.8 mg
CuSO$_4$.5H$_2$O: 0.5 mg
Na$_2$MoO$_4$.2H$_2$O: 0.48 mg
CoCl$_2$.6H$_2$O: 0.48 mg
MnSO$_4$.5H$_2$O: 2.4 mg
Distilled water: 1 l A culture medium (100 ml) consisting of the above ingredients was placed into a 0.5-l Sakaguchi flask, and sterilized at 120° C. for 15 minutes. Then, 0.2 g of methanol was sseptically added. Into the resulting culture medium was inoculated 0.5% by volume of a pre-culture containing the cells of *Corynebacterium yamanasiensis* DS-31 (FERM-P No. 4106) which had been obtained by pre-cultivation at 35° C. for 24 hours in a culture medium having the same composition as above except that the amount of methanol added was changed to 0.5% by weight. Cultivation was performed with shaking at 35° C. for 24 hours. The culture broth was centrifuged to separate the microbial cells. The cells were washed with water, and dried at 100° C. for 24 hours to afford 0.84 g of dried cells per liter of the culture broth. The generation time of this culture in the logarithmic growth period was 1.5 hours. The cells were found to contain 76% by weight of crude proteins.

EXAMPLE 12

A culture medium (500 ml) having the same composition as in Example 11 except that the amount of methanol was changed to 5 g was placed into a 1-l small jar, and sterilized at 120° C. for 15 minutes. Then, methanol in the above-indicated amount was added aseptically. Into the resulting culture medium was inoculated 2% by volume of a pre-culture containing the cells of *Corynebacterium yamanasiensis* DS-31 (FERM-P No. 4106) which has been obtained by pre-cultivation at 37° C. for 24 hours in a culture medium having the same composition as above. Cultivation was performed with aeration and stirring at 37° C. for 20 hours while maintaining the pH of the culture medium at 7.0 by using 13% by weight ammonia solution.

The culture broth was centrifuged to separate the microbial cells. The cells were washed with water, and dried at 100° C. for 24 hours to afford 4.0 g of dried cells per liter of the culture broth. The generation time of this culture in the logarithmic growth period was 1.6 hours. The cells were found to contain 77% by weight of crude proteins.

What is claimed is:

1. A process for producing microbial cells which comprises cultivating the bacterium *Flavobacterium tosaensis* DS-1 (FERM-P No. 4058) in a culture medium containing methanol as a major carbon source, and recovering the microbial cells from the culture broth.

2. A process for producing microbial cells which comprises cultivating the bacterium *Flavobacterium methanolicola* DS-16 (FERM-P No. 4098) in a culture medium containing methanol as a major carbon source, and recovering the microbial cells from the culture broth.

* * * * *